United States Patent [19]
Spurgeon

[11] Patent Number: 5,890,129
[45] Date of Patent: Mar. 30, 1999

[54] SYSTEM FOR EXCHANGING HEALTH CARE INSURANCE INFORMATION

[76] Inventor: Loren J. Spurgeon, 521 16th Ave. West, Kirkland, Wash. 98033

[21] Appl. No.: 865,719

[22] Filed: May 30, 1997

[51] Int. Cl.⁶ ...................................................... B42D 1/10
[52] U.S. Cl. ................ 705/4; 705/2; 705/3; 395/200.32; 395/200.47; 707/1; 707/10; 707/102
[58] Field of Search .................. 705/2, 3, 4; 395/200.32, 395/200.47, 200.33; 707/1, 10, 102, 200

[56] References Cited

U.S. PATENT DOCUMENTS 5,664,109 9/1997 Johnson et al. ............................. 705/2

*Primary Examiner*—Thomas R. Peeso
*Attorney, Agent, or Firm*—Kolisch, Hartwell, Dickinson, McCormack & Heuser

[57] ABSTRACT

An information-exchange system is provided for controlling the exchange of business and clinical information between an insurer and multiple health care providers. The system includes an information-exchange computer that is connected over a local area network to an insurer computer using a proprietary database and over the Internet to health-care provider computers using open database-compliant databases. The information-exchange computer receives subscriber insurance data from the insurance computer database, translates the insurance data into an exchange database, and pushes the subscriber insurance data out over the Internet to the computer operated by the health-care provider assigned to each subscriber. The information-exchange system stores the data in the provider database. The information-exchange system also provides for the preparation, submission, processing, and payment of claims over the local area network and with push technology over the Internet. In addition, prior authorization requests may be initiated in the provider computers and exchanged over the information-exchange system for review by the insurer computer. Processed reviews are transmitted back to the provider computer and to a specialist computer, if required, using push technology over the Internet.

24 Claims, 16 Drawing Sheets

Member Demographics Information

MEMBER

| Member Number | SSN (if different) | | | | |
|---|---|---|---|---|---|
| Member-Last Name | First | M. I. | Age | Sex | DOB |

Home Address

| Home Address-Line 2 | City | ST | Zip |

| Home Telephone | Work Telephone |

EMPLOYER

Employer Name

| Employer Address | City | ST | Zip |

| Employer Phone Number | Group Number | Plan Number |

DEPENDENTS

| Dependent 1-Last Name | First | MI | Age | Sex | DOB |
| Dependent 2-Last Name | First | MI | Age | Sex | DOB |
| Dependent 3-Last Name | First | MI | Age | Sex | DOB |
| Dependent 4-Last Name | First | MI | Age | Sex | DOB |
| Dependent 5-Last Name | First | MI | Age | Sex | DOB |
| Dependent 6-Last Name | First | MI | Age | Sex | DOB |

Fig. 5

Benefit Package Information

| | | | |
|---|---|---|---|
| Member Number | Member Name | Patient Name | Patient SSN |

| BENEFIT DESCRIPTION | CO-PAY |
|---|---|
| PCP Office Visit | $ 10.00 |
| Specialist Office Visit | $ 0.00 |
| Prescription Drugs | $ 5.00 |
| Inpt Room and Board | $100.00 |
| Inpt Mental Health | $ 30.00 |
| Opt Mental Health | $ 15.00 |
| Inpt Substance Abuse | $ 30.00 |
| Opt Substance Abuse | $ 15.00 |
| Hosp Emergency Room | $ 35.00 |
| Urgent Care Center | $ 10.00 |
| Home Health/Hospice/RN | $ 10.00 |
| Spinal Benefit | $ 10.00 |

Fig. 6

Eligibility Information

| | | | |
|---|---|---|---|
| Member Number | Member Name | Patient Name | Patient SSN |

ELIGIBILITY INFORMATION

| Employer | Eligibility Type | |
|---|---|---|
| Group Number | Effective Date | Expiration Date |

| Employer | Eligibility Type | |
|---|---|---|
| Group Number | Effective Date | Expiration Date |

| Employer | Eligibility Type | |
|---|---|---|
| Group Number | Effective Date | Expiration Date |

Notes

Fig. 7

Primary Care Physician (PCP) Assignment

| Member Number | Member Name | Patient Name | Patient SSN |

PCP ASSIGNMENT

| PCP Assigned | Specialty | Provider Number | EIN Number |

Location 1

| Group Name | Group Provider Number | | Group EIN Number |
| Address | City | ST | Zip |
| Telephone | FAX | | |

Location 2

| Group Name | Group Provider Number | | Group EIN Number |
| Address | City | ST | Zip |
| Telephone | FAX | | |

Location 3

| Group Name | Group Provider Number | | Group EIN Number |
| Address | City | ST | Zip |
| Telephone | FAX | | |

Fig. 8

Claim Submission

HEALTH INSURANCE CLAIM FORM

Fig. 9

Prior Authorization Information

Demographics
Benefits
Provider
Referred To
Codes
Services
Sending To

Demographics from

Member Demographics Screen

Fig. 10

Prior Authorization Information

Demographics
Benefits
Provider
Referred To
Codes
Services
Sending To

Benefits from

Benefit
Package
Screen

Fig. 11

Prior Authorization Information

Demographics
Benefits
Provider
Referred To
Codes
Services
Sending To

Provider Information from the

Provider Database in the Marimba Application

Fig. 12

Prior Authorization Information

Demographics
Benefits
Provider
Referred To
Codes
Services
Sending To

Referred To
Information from the

Health Plan
Provider
Network
Database
(Chosen from a
Search Screen)

Fig. 13

Prior Authorization Information

Demographics
Benefits
Provider
Referred To
Codes
Services
Sending To

Codes

ICD9          Description

CPT          Description

HCPCs        Description

Fig. 14

Prior Authorization Information

Demographics
Benefits
Provider
Referred To
Codes
Services
Sending To

Services and Dates

DATES

Onset  Encounter  Service

Admission  Procedure

Days or Visits

Requested  Approved  Actual

Place of Service

Type of Admission

Fig. 15

Prior Authorization Information

Demographics
Benefits
Provider
Referred To
Codes
Services
Sending To

Sending To

Department

Fig. 16

SYSTEM FOR EXCHANGING HEALTH CARE INSURANCE INFORMATION

FIELD OF THE INVENTION

The present invention relates generally to a computerized system that controls the exchange of business and clinical information necessary for efficient administration of services in a health care delivery system. More specifically, it concerns a computerized system for controlling the exchange of subscriber demographics, benefit plan, eligibility, prior authorization, claims, quality assurance and governmental regulatory information between an insurance company and multiple health care provider groups.

BACKGROUND

Costs of health care in the U.S. and elsewhere have been increasing dramatically in recent years, at least in part due to advances in medical technology which call for more expensive surgery and treatment regimes and complex diagnostic and therapeutic procedures. To control these escalating costs, insurers have developed a managed care model for health care insurance wherein the insurers' subscribers, i.e., health care consumers, pay a lower insurance premium in exchange for the insurers' assuming a greater degree of control over the provision of health care.

In the managed care model, insurers negotiate fee schedules with medical service providers. Furthermore, each insurer checks the credentials of health care providers before approving them to provide service under the insurer's health plan. The group of credentialed providers is referred to as a Network or Panel and may consist of hundreds of providers. As used herein, provider refers to a doctor or other health care provider, or groups thereof practicing together as a business entity. Each provider may belong to several Networks so that the provider can accept patients who subscribe to various insurance plans.

The insurers may additionally or alternatively manage care by paying a greater portion of the claim when the subscriber uses a preferred provider, or by requiring the subscriber to initiate care at the subscriber's primary care physician. After providing health services, the primary care provider or preferred provider submits a claim to the insurer.

When a primary care provider or preferred provider recommends surgery or special treatment outside the scope of services available at its office, the insurer, in a managed care system, requires that advance authorization be obtained through a process known as prior authorization or pre-certification. Prior authorization may also be required for some services provided by the primary care provider. If the proper authorization is not obtained beforehand, the insurer may deny coverage. The insurer may deny a claim for past treatment or a prior authorization for future treatment when the treatment is beyond the insurance coverage of the subscriber or not medically appropriate for the subscriber. Thus, under managed care, the insurer must carefully monitor the course of treatment recommended by the providers.

In operation, the managed care model requires constant exchange of large amounts of information between insurers and providers because the insurer tracks each subscriber's benefit plan, symptoms, diagnoses, treatment and other information to determine if the claims made by health care providers are covered and conform to actuarial guidelines of medically appropriate treatment regimens. Confusion and delay in the processing of such information are frustrating to all parties involved—treatment is delayed to subscribers; payments are delayed to providers; and dissatisfied subscribers complain to their insurers and/or cancel their coverage. Ultimately, dissatisfied providers may opt out of the insurer's Network.

The potential for confusion and delay is heightened by the present limitations on the exchange of the information. In particular, each organization has a computerized system handling the particular requirements of the organization, but, unfortunately, these systems are not directly compatible. A subscriber enrolls in a health insurance plan, typically through the subscriber's employer, by providing demographic information to the health plan. These demographics, or enrollment data, are keyed into the insurer's computer system software application, referred to as a Healthcare Information System (HIS), and are then associated with a benefits package, eligibility information and Primary Care Provider (PCP) assignment. When the subscriber goes to a provider's office seeking health care, the subscriber must again provide the demographics to the provider who checks, by telephone or fax, the records of the insurer to verify eligibility. The provider manually enters these same demographics into their computer system, often referred to as a Practice Management System (PMS) application, consuming time and money and risking data-entry error. Another bottleneck in the exchange of information occurs when the provider determines that special treatment is required that must be pre-authorized pursuant to a utilization review. The provider prepares the prior authorization request and sends it to the insurer or a third party review agency by telephone, mail or fax. The insurer returns prior authorization approval or denial by the same inefficient, error-prone route.

The HIS system typically includes large, complex software applications costing from $300,000 to $1,000,000 and utilizes a proprietary database running on a midrange computer system such as IBM's AS/400. The providers typically use one of numerous, mutually incompatible PMS applications, many of which run on outdated Unix systems, although some are PC-based. Generally, each insurer's HIS is unique to that insurer and of the numerous PMS applications available, no single product has a significant market share. Each insurer deals with hundreds of providers and each provider deals with perhaps dozens of insurers. The differing operating systems and database structures within the applications prevent the direct transfer of information therebetween. The insurers and providers, each with their own separate island of information, are required to enter manually the same information repeatedly as the subscriber's case navigates among the islands of enrollment, care provision, prior authorization, claims, etc.

It is likely that these islands of information will persist despite the overall cost to the organizations as a whole because of each insurer's investment in their proprietary HIS software and databases and the competitive and non-standardized nature of the market for PMS applications. There are some integrated insurance and medical organizations which bring the islands of information under a one-world model where the insurer and all the providers work for one company and use common standardized data sets in all of their applications. This model, while potentially offering improved efficiency, is inadequate for two reasons. First, the subscribers still frequently require medical care outside the integrated companies either due to an emergency or specialized care that the benefits package covers. Second, this system is of no help to the many separate insurance and medical companies, which will persist for the foreseeable future in the free market. A need therefore exists for a system that allows the insurers and providers to continue to use their existing applications and, at the same time, reap the benefits of automatic exchange of insurance information.

SUMMARY OF INVENTION

The present invention is a system of exchanging clinical and business information, within the existing environment of disparate hardware and software, in a standard format over a standard transmission medium. The hub of the system is an exchange database located on a computer which will be referred to as a web server or information-exchange computer. The invented information-exchange system includes the information-exchange computer, as well as software applications that run on the web server and other "client" computers located at the providers' and the insurers' offices. The information-exchange system relies on the Internet, or direct dial up access, and Local Area Networks (LANs) to transmit information which the system has translated and reformatted. The information may be translated at the client or at the information-exchange computer, into a standard format.

The present invention is probably most easily understood by reference to an example of the system operation. Initially, the subscriber purchases insurance coverage from an insurer. The subscriber provides data to the insurer including eligibility dates and demographic information, e.g., name, address, employer and dependents, and selects a primary care provider. The insurer enters the demographic and eligibility data into the insurer's preexisting HIS software application and database and assigns a benefit package. The subscriber insurance data is imported over a LAN connection into the database on the web server. The subscriber insurance data is then transmitted to the primary care provider's PC over the Internet, or dial up access, using push technology that automatically broadcasts the data to the PC without further human intervention. At the provider's PC, the provider may view the transmitted information using an appropriate "client" software package, such as a browser. A provider interface portion of the information-exchange system running on the provider's PC also translates and reformats the information for the provider's specific PMS application and transmits it over a LAN to the computer running the PMS application.

The information-exchange system eliminates the need for manual reentry of subscriber insurance data at the provider's office. With the information-exchange system, the subscriber need only show an insurance card to the provider who can then immediately check the enrollment, benefit plan and eligibility information already resident in the information-exchange system and in the provider's PMS application.

After providing health care services to the subscriber, the provider normally processes a claim using its PMS application. The claim is then transmitted to the provider's information-exchange interface computer where a client application, i.e., a provider interface portion, of the information-exchange system translates and reformats the claim. For the providers who do not have a legacy PMS application, i.e., a PMS application in which the provider has invested money and employee training that the provider does not wish to write-off, the provider interface portion allows the direct entry of claim information at the provider's office. The provider interface portion then transmits the claim up to the web server and there it is translated, reformatted and transmitted via push technology to the insurer's HIS or to a third party claim processor. This automatic exchange replaces the prior system of the providers' printing out the claims and mailing or faxing the printed claims to the insurer for manual reentry.

If the primary care provider determines that treatment by a specialist or exceptional treatment by the provider is indicated for the subscriber, a prior authorization request is submitted, in order to request a utilization review of the proposed treatment. The insurer previously would receive the requests by telephone, mail or fax. Using the provider interface portion of the information-exchange system, the provider enters information necessary for a prior authorization on the provider interface computer. The information-exchange system transmits, via push technology, the information up to the web server, which transmits the information to the insurer and/or to a third party review agency. In the course of this transmission, the information-exchange system translates and reformats the information as required for the receiving utilization review software, which may be running on the insurer's or third party review agency's computer. The utilization review software processes the prior authorization request to aid the insurer or third party review agency in determining the subscriber eligibility and the medical appropriateness of the prior authorization request.

When the insurer or the third party review agency completes the processing of the information, the information-exchange system receives the authorized or denied request and translates and reformats this data for the exchange database. If the request is approved for specialist treatment, the information-exchange system then transmits the review to a specialist provider interface computer at the specialist's office which translates and reformats the reviews for the specialist's PMS. The reviews, both approved and disapproved, are also transmitted to the original health care provider.

When integrating computers that use mutually incompatible databases, the information-exchange system can be visualized as a hub-and-spoke system with the information-exchange computer forming the hub. Spokes of the system extend out from the hub along the Internet, dial up access, or LANs to PC's and mid-sized computers operated by providers and insurers. Each spoke provides for the translating, reformatting, transmission and receipt of the information contained in the provider's or insurer's specific database. The information-exchange system may also include direct communications between provider interface computers and insurer computers when the databases are directly compatible.

A main advantage of the information-exchange system is the increased speed with which claims are processed and paid and with which a subscriber may learn if a requested treatment will be paid for by the insurer. The replacement of fax, telephone and mail with a high-speed, computerized system as a continuous conduit for all aspects of these requests produces the increased speed.

Opportunities for errors and miscommunications are also eliminated by the information-exchange system of the present invention. Updates are made directly, accurately and automatically by the software used by the insurers and providers without a requirement for manual reentry of information.

Another advantage of the present invention is that the provider need not be concerned with what HIS is used by the insurer, and the insurer is likewise unconcerned with the PMS of the provider. The providers and insurers can transmit clinical and business information back and forth automatically without having to translate directly between the incompatible databases. The information-exchange system provides for a common language for all while still permitting each to use the proprietary system of their choice.

These and other objects and advantages of the invention will be more fully understood by reference to the accompanying drawings and the detailed description to follow.

BRIEF DESCRIPTION OF THE DRAWINGS

FIG. 5 is a data screen provided by the information-exchange system for entry or review of subscriber demographics.

FIG. 6 is a data screen provided by the information-exchange system for entry or review of benefit package information.

FIG. 7 is a data screen provided by the information-exchange system for entry or review of eligibility information.

FIG. 8 is a data screen provided by the information-exchange system for entry or review of primary care physician assignment.

FIG. 9 is a data entry screen provided by the information-exchange system for entry and submission of claims.

FIG. 10 is a data screen provided by the information-exchange system for entry or review of subscriber demographics during prior authorization entry.

FIG. 11 is a data screen provided by the information-exchange system for entry or review of benefits package during prior authorization entry.

FIG. 12 is a data screen provided by the information-exchange system for entry or review of provider information during prior authorization entry.

FIG. 13 is a data screen provided by the information-exchange system for entry or review of referred-to information during prior authorization entry.

FIG. 14 is a data screen provided by the information-exchange system for entry or review of codes information during prior authorization entry.

FIG. 15 is a data screen provided by the information-exchange system for entry or review of services and dates information during prior authorization entry.

FIG. 16 is a data screen provided by the information-exchange system for entry or review of sending-to information during prior authorization entry.

DETAILED DESCRIPTION OF THE PREFERRED EMBODIMENT

Figure 1:
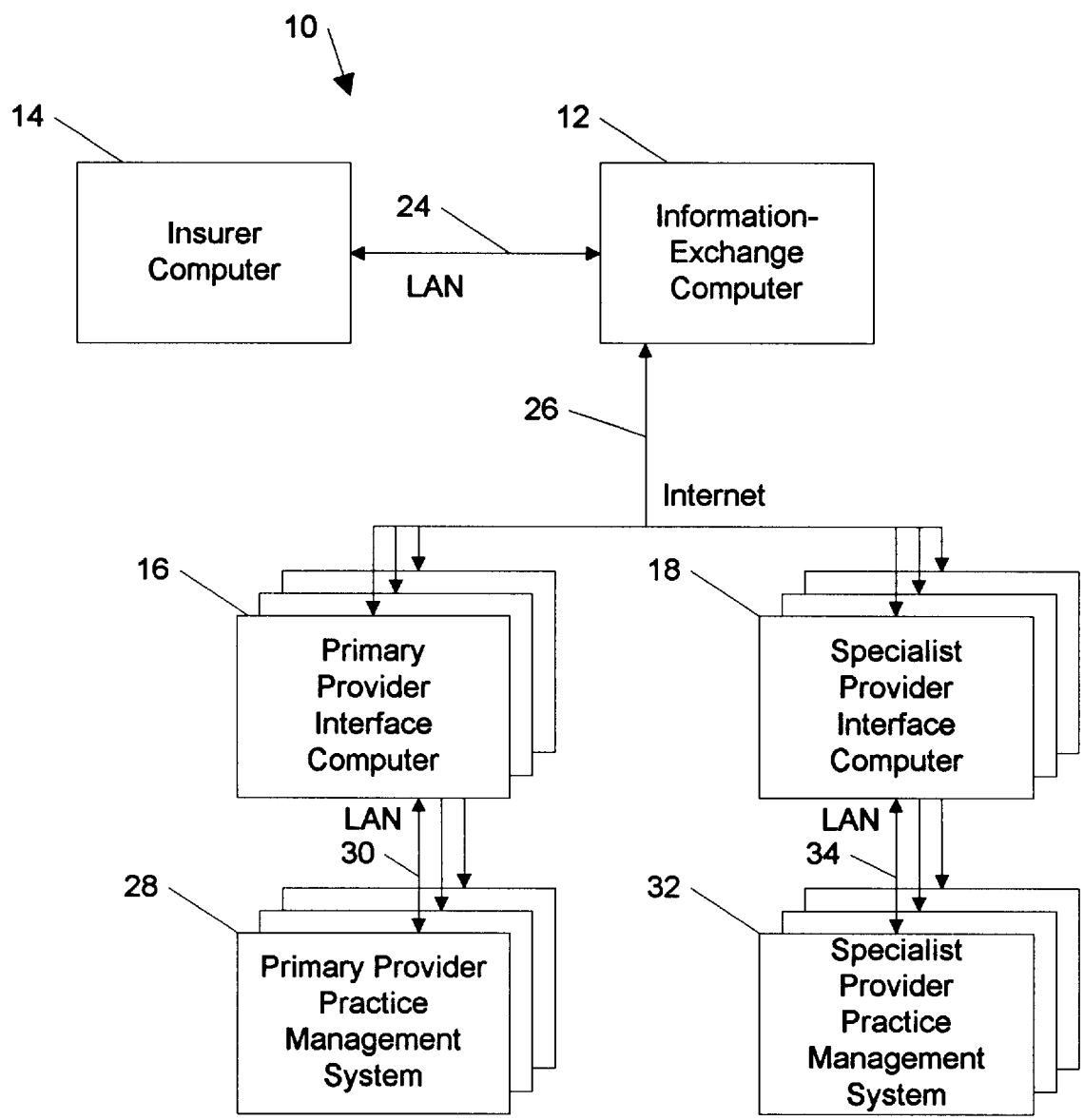
FIG. 1 is a system diagram of the information-exchange system showing the interconnection of the computers in the system.

The present invention is an information-exchange system, shown generally at 10 in FIG. 1, which provides for the processing of health-insurance data over local area networks, the Internet, through dial up access, satellite uplink or any other network using an open communications protocol, such as TCP/IP. The system includes an information-exchange computer 12, also referred to as a web server, local information-exchange software operable on that computer, and, in some cases, remote information-exchange software operable on client computers. The invented system integrates the operation of the client computers which include insurer computers 14, primary health care provider interface computers 16 and specialist health care provider computers 18. The insurer computer may be replaced by third party computers which provide for claims processing and review of prior authorization requests. The insurer computer or the third party computer and the information-exchange computer are preferably both capable of communicating on, and are interconnected by, an insurer local area network 24. The provider interface computers and the information-exchange computer are preferably capable of communicating on, and are interconnected by, the Internet 26 or dial up access over a POTS (Plain Old Telephone Service) line. The insurer or third party claim processor and review agency computers may alternatively be connected to the information-exchange computer either by the Internet or dial up access.

Figure 2:
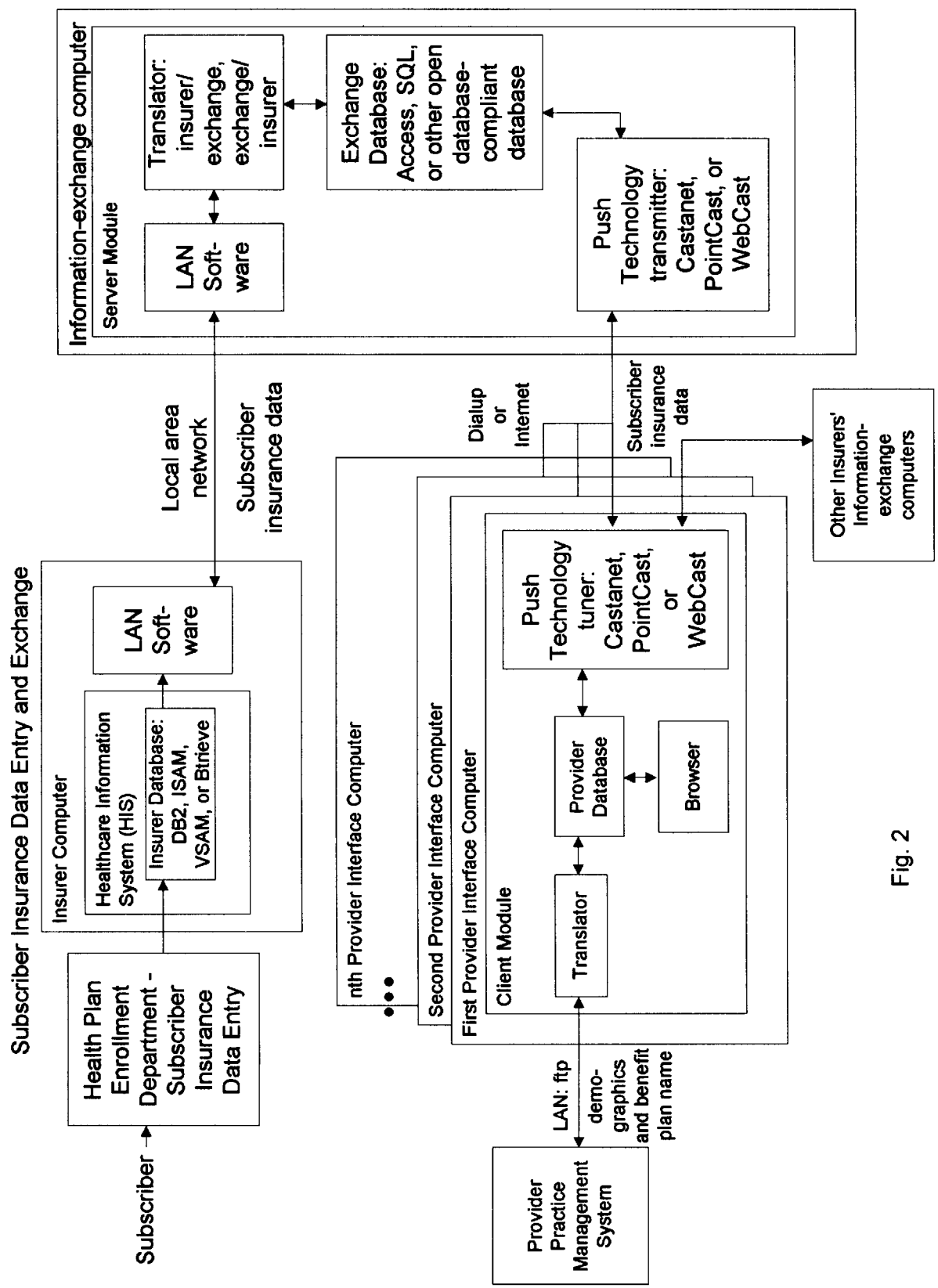
FIG. 2 is a system flow diagram of the information-exchange system showing processing and exchange of subscriber insurance data.
Figure 3:
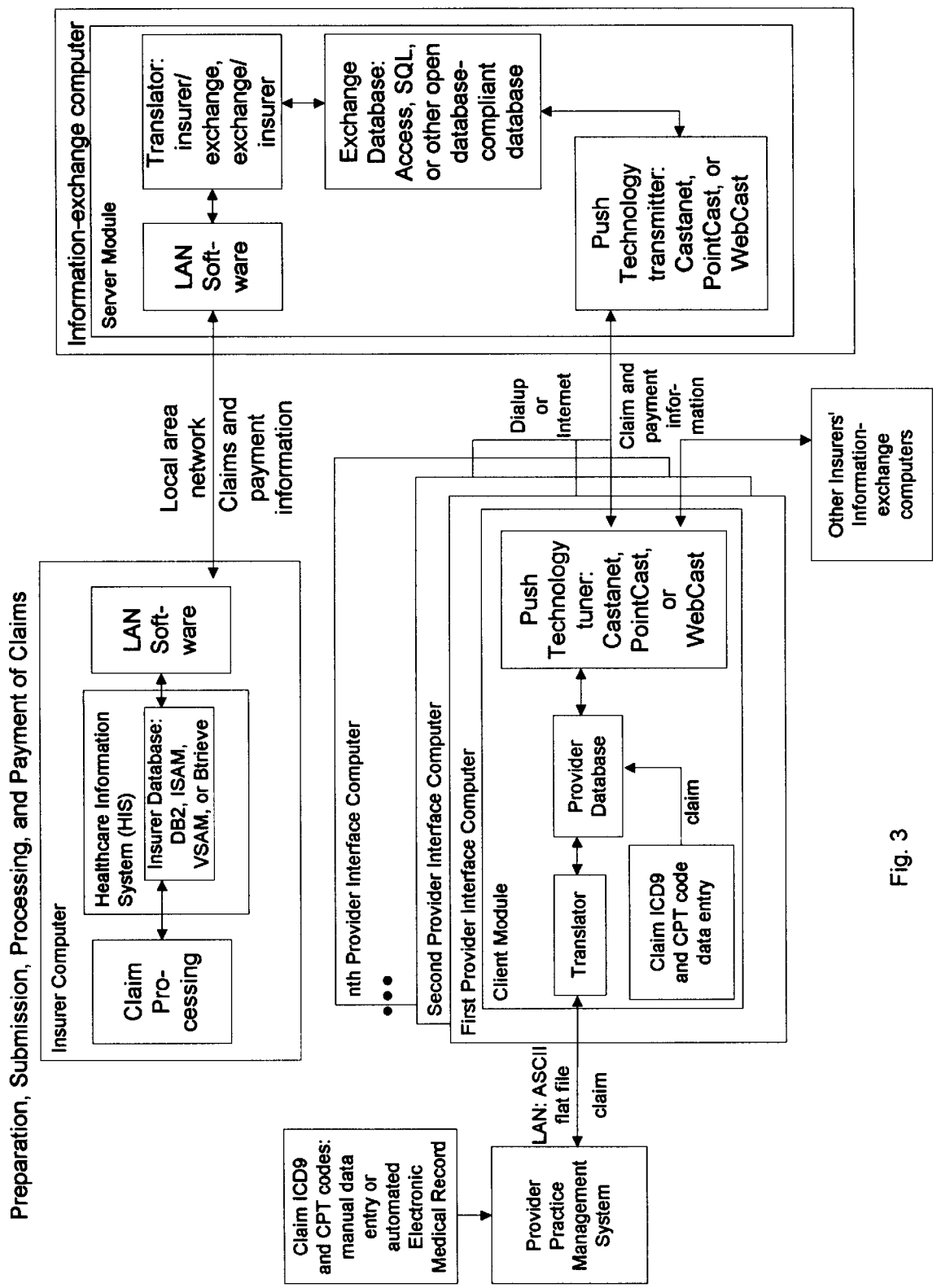
FIG. 3 is a system flow diagram of the information-exchange system showing processing and exchange of a claim.
Figure 4:
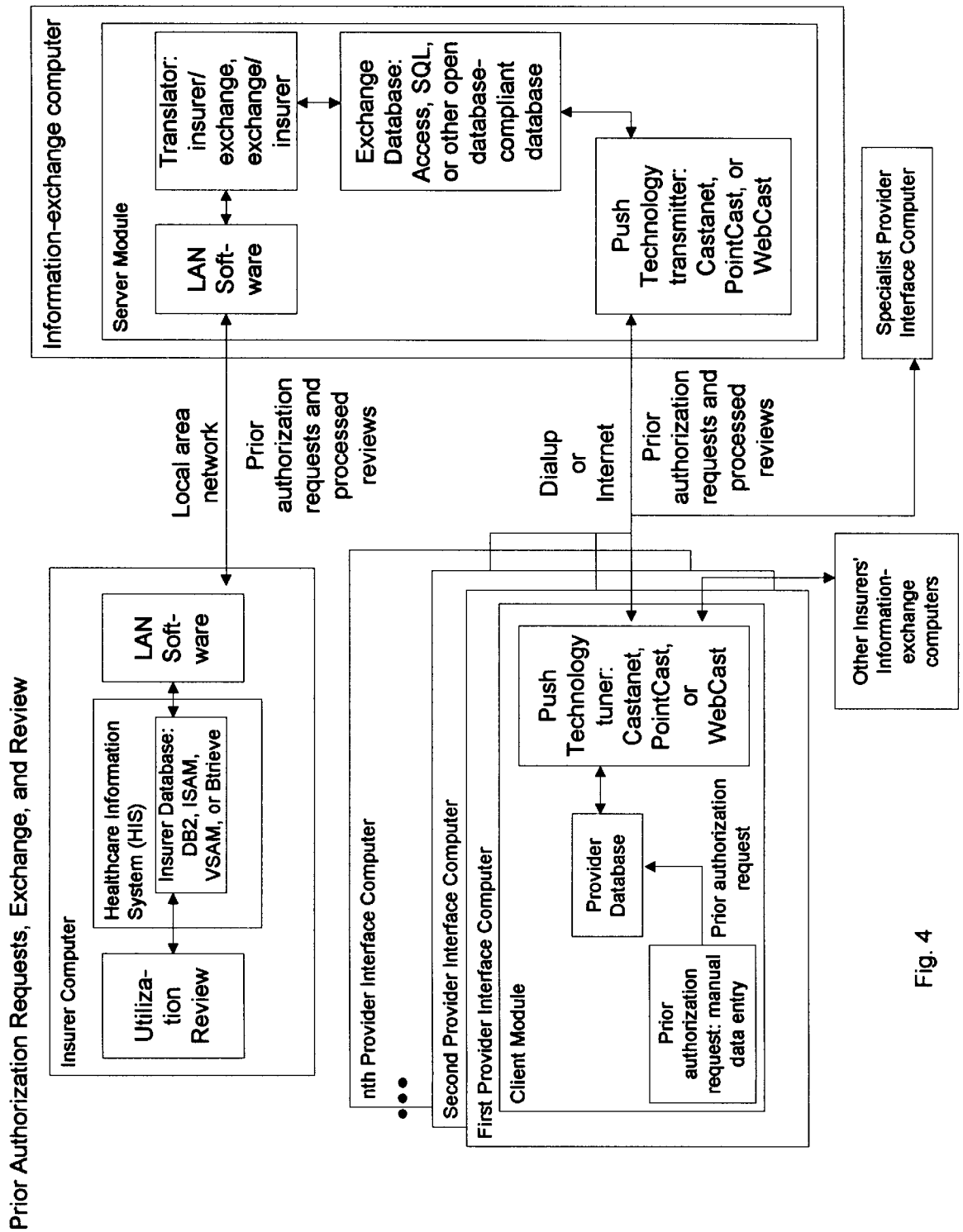
FIG. 4 is a system flow diagram of the information-exchange system showing processing and exchange of a prior authorization request and review.

The computers are integrated for the performance of three main functions: (1) enrollment of subscribers; (2) submission and processing of claims; and (3) preparation and processing of prior authorization requests. These functions are depicted in FIGS. 2, 3 and 4, respectively. In addition, the provider may use data screens available on the provider interface computers, such as shown in FIGS. 5–8, for confirmation of benefit plan and eligibility of subscribers.

As shown in FIG. 2, enrollment begins with a subscriber obtaining insurance coverage from an insurer and providing data to a health plan enrollment department. Subscriber insurance data is then entered into a Healthcare Information System (HIS) software application operable on the insurer's computer. The subscriber insurance data includes information on subscriber demographics or enrollment data, eligibility, selected benefit package and selected primary care provider. A typical data screen for demographics, used by the health plan enrollment department during data entry, includes fields for subscriber (or member) number, name, address, employer, dependents and other information, as shown in FIG. 5. A typical data screen for benefit package information is shown in FIG. 6. Eligibility information is entered on a data screen such as that shown in FIG. 7. A data screen, such as that shown in FIG. 8, provides for assignment of a primary care physician that the subscriber has selected from a list of credentialed doctors.

Subscriber insurance data for a group of subscribers is stored on the insurer computer in an insurer database. The insurer has multiple health care providers for the group of subscribers. A subgroup of subscribers is assigned to each one of the health care providers. The information-exchange system is designed to be adaptable to any insurer computer in the present or future marketplace. These insurer computers may be mainframe computers, or more typically a midrange computer such as IBM's AS/400. The insurer database is part of the HIS application, which is a large, complex software application accessible by many other departments of the insurer in addition to the enrollment department. The insurer database is typically in a predetermined format, such as DB2, VSAM, ISAM or Btieve, which is proprietary and unique to each insurer. Nonetheless, the information-exchange system is adaptable to any insurer database by customizing a translator which provides an interface between the proprietary insurer database and the information-exchange computer's database.

LAN software is installed on the insurer computer to enable it to communicate over an insurer local area network as depicted in FIG. 1. The LAN software may be part of the HIS, provided separately or provided as part of the information-exchange system when not available otherwise. The local area network provides a conduit for the subscriber insurance data to be transmitted to the information-exchange computer. The information-exchange computer includes LAN software making it capable of communicating on the local area network to receive the subscriber insurance data. Although the local area network is preferably a network such as an Ethernet or token ring network, as is typically used by the HIS, it will be understood that a simple se rial channel connection or modem line could be used as well.

The information-exchange system includes software installed and operable on the information-exchange computer or web server. This software is referred to as a server module and includes a translator which makes database requests to the insurer database and imports the resulting data, automatically translating the data for storage in an exchange database located on the information-exchange computer. The translator is customized to accommodate the particular insurer database format in use.

The exchange database is preferably stored in a predetermined open database-compliant or ODB-compliant format different from the format of the insurer database. ODB-compliant databases include those developed using database standards or programs such as Access, SQL and others. Economy in programming costs is obtained by making the exchange database in a single configuration that can be made to be compatible with any insurer and any provider by appropriate translators for automatically reformatting the incoming data. The insurer database is typically neither an SQL database nor ODB-compliant.

The information-exchange computer is capable of communicating either through the Internet at a high bandwidth or through a bank of modems for dial up access to speed communications with a large number of health care providers. The subscriber insurance data is preferably broadcast out to the appropriate providers using push technology.

Each provider that accepts patients from the insurer is furnished with an interface computer, e.g., a PC, capable of sustaining an Internet Protocol (IP) address to permit communication through the Internet or capable of dial up access. The interface computer may alternatively be any hand-held device capable of a modem or satellite uplink connection to the Internet, i.e., any device capable of sustaining an IP address. The provider interface computer forms a part of the information-exchange system, referred to as a client module or the provider interface portion.

Push technology is used to transmit information between the information-exchange computer and the provider interface computer. Push technology is a method of communication employed by a server computer to communicate with a client computer. This technology may be conducted over an internally hardwired network (i.e., a Local Area Network with Category 5 wiring using a 10BaseT Ethernet scheme), across a dial up network via modem access (Wide Area Network) or through the Internet.

The push method begins with the installation of a client software application, which is used by the server to identify the client on the network. The client also uses this application as a subscribing device to order customized information. The user of the client application enters requests for specific classes of information and preferred frequency of updates.

After receiving this user specific information, the server fashions a response based upon inherent features of the server application and the user requests. The server then pushes the customized information across the network to the client, hence the name push technology.

Push technology ensures that the data on the provider interface computer is always kept up-to-date because the data is pushed out to the provider interface computer and into a provider database located therein rather than requiring the provider to pull the data down from the information-exchange server. Push technology as implemented in the information-exchange system includes three components: channels, which are applications or information which are distributed across the Internet, dial up network, or LAN; an application running on the information-exchange computer which manages the distribution and maintenance of the channels; and an application on the provider interface computers which monitors, receives and manages the channels. In the information-exchange system, an application pushed as a channel is operable on the provider interface computers to make entries, modifications and deletions within the provider database using information which has also been distributed as a channel.

The push technology on the information-exchange computer is preferably a Castanet™ transmitter, produced by Marimba™. The provider interface computer includes a complementary tuner to receive the subscriber insurance data for storage in the provider database. Push technology is also available from PointCast™ and WebCast™. The push transmitter has a built-in capability to encrypt data and sends the encrypted subscriber insurance data, either over the Internet or through dial up access, to the subscriber's assigned Primary Care Provider (PCP) whose provider interface computer is tuned to receive that data. The transmitter also sends an application over the Internet or through dial up access, such as a Java applet, that is operable on the provider interface computer to decrypt and store the subscriber insurance data in the provider database. The tuner also has the capability to encrypt and push data to the transmitter. As seen in FIG. 1, a plurality of provider interface computers may be connected to the information-exchange computer over the Internet or through dial up access. These provider interface computers may also receive subscriber insurance data from, and communicate with, other information-exchange computers operated by other insurers whose coverage the providers are authorized to accept. Each provider interface computer stores the subscriber insurance data in its own provider database.

In addition to the new subscriber scenario, other situations will arise in which the data for the subgroup of insurance subscribers in each provider database should be updated. For instance, an existing subscriber may choose to change primary care providers in which case a deactivation message is broadcast to the old provider and subscriber insurance data is broadcast to the new provider. Also, when an insurer credentials new providers, the new provider is typically assigned a batch of previously unassigned subscribers. The subscriber insurance data for all of the subscribers is broadcast out to the newly-credentialed provider. Push technology is used in all of these situations to broadcast the subscriber insurance data to the providers. One major advantage of the invented system is that the provider is kept up-to-date on patient/subscriber status without any direct intervention on the part of the provider.

The provider may also have a pre-existing practice management system (PMS), which is an application that may be operable on a separate practice management computer, shown at 28 in FIG. 1, or, in some cases, on the provider interface computer. In a large office of providers, the practice management system computer may be an RS6000, while in a small office it may be a 286-based PC. With the PMS installed on a practice management computer, the provider interface portion automatically translates the enrollment demographics and benefit plan name and transmits it over a provider local area network 30 to the practice management computer. Preferably, in a Unix-based PMS, such as are common, this transmission makes use of file transfer protocol, or ftp.

Thus, when the subscribers arrive at their chosen provider's office, the subscriber insurance data is already available and current at the office and does not need to be reentered or remotely checked via telephone. The provider may review the subscriber's data using appropriate software installed on the provider interface computer or using the PMS. In addition, if the subscriber discovers at the provider office that some subscriber demographics in the provider database are incorrect either because of a data entry error at the insurer or change to the subscriber's circumstances, changes to the database may be made to the provider database. The tuner in the client application will then push the changed information to the transmitter on the information-exchange computer for entry into the exchange database and ultimately the insurer database.

In the information-exchange system, the translator installed on the information-exchange computer makes it possible to have automatic transmission of subscriber insurance data between the insurer and provider even when the insurer database and the provider database are mutually incompatible. The insurer database may have any unique or proprietary format. The provider database is preferably ODB-compliant which is typically incompatible with proprietary formats. The various provider PMSs also typically use unique data formats, most of which are incompatible with one another. The provider interface portion on the provider interface computer allows communication between the information-exchange computer and any PMS despite the differing data formats because the provider interface portion can provide an appropriate customized translation for each PMS format.

Figure 9:
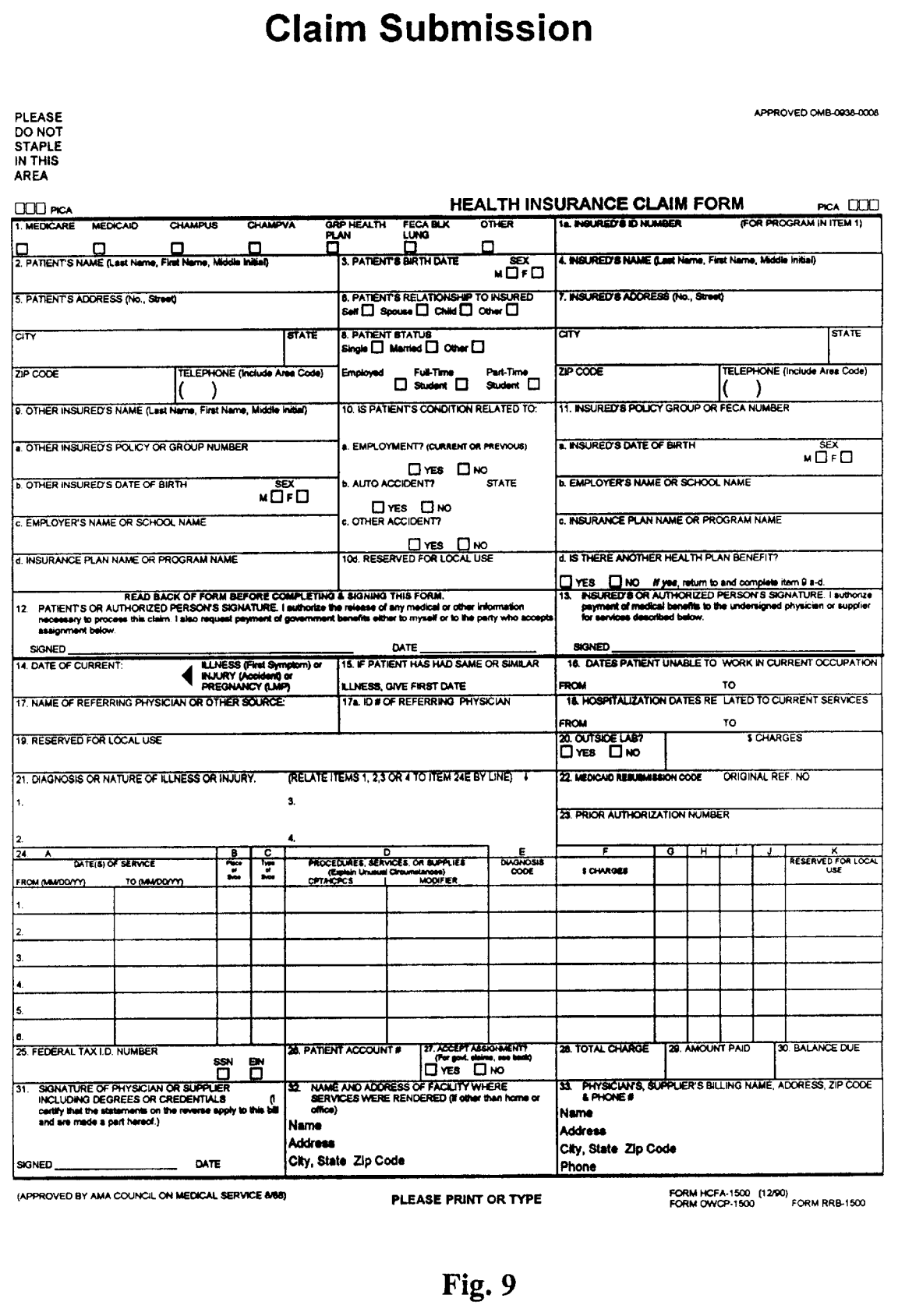

The preparation, submission and processing of claims with the information-exchange system is depicted in FIG. 3. For providers with a legacy practice management system, entry of claims remains the same. In particular, the existing PMS is used to enter the International Classification of Diseases (ICD9) and Clinical Procedure Terminology (CPT) codes that represent the diagnoses and treatments of the patient-subscriber, respectively. The entry may be manual or an Electronic Medical record device may be used to automatically enter claims. Preferably, claims entered in this manner and assembled by the PMS are transmitted over the provider local area network as an ASCII flat file to the provider interface portion of the information-exchange system. Providers not using an existing PMS may enter claims information directly manually, on the provider interface computer using a claim data entry interface in the provider interface portion that replicates some features of a PMS or with an Electronic Medical record device. A data entry screen for claims is shown in FIG. 9. For claim entry either through the PMS or the provider interface portion, the provider interface computer receives the claims and stores the claims in the provider database.

In the preferred embodiment, the provider interface computer transmits the claims, either over the Internet in encrypted fashion or through dial up access, to the information-exchange computer. Preferably, the tuner in the client application encrypts and pushes the claims to the transmitter in the information-exchange computer. As seen in FIG. 3, multiple provider offices with PMS and provider interface computers are capable of transmitting to the information-exchange computers. Because each provider may have patients from several insurers, each of whom have their own information-exchange computer, the provider interface computer must be able to transmit claims to multiple information-exchange computers.

The transmitted claim is stored in the exchange database and translated for transmission to the insurer or to a third party claim processor's or administrator's computer. Transmission to the insurer's or third party's computer is preferably conducted over the insurer local area network. However, the transmission, especially to the third party's computer, which in some cases may be located offsite, may be done either over the Internet or through dial up access. It will be understood that a third party's computer is typically provided with network communication capabilities and a third party database equivalent to the insurer database on the insurer's computer and that transmission to the third party database, over a local area network, the Internet or through dial up access, is similar to transmission to the insurer database over the insurer local area network.

The insurer or administrator computer receives the claim and stores it in the insurer database. Once the claims processing department receives the claim, the staff verifies the member's eligibility, confirms the benefit package, and, for specialist provider claims and other claims requiring prior authorization, accesses a prior authorization module of the HIS application. The ICD9 codes, CPT codes and the approval number in the approved prior authorization request must identically match those stipulated in the claim. If an identical match exists, or if the claim is covered by the benefit package without prior authorization, the staff member in the claims processing department approves the claim and initiates payment. The amount of payment is determined by the CPT codes and their associated payment scheduled contained in the provider's contract.

Initiation of payment procedures by the claims processing staff originates an electronic payment. This electronic payment transaction is communicated over the network connection to the information-exchange computer. The information-exchange computer first configures the electronic payment and the accompanying documentation. Then, the information-exchange computer transmits the electronic Explanation of Benefits (EOB) to the provider interface computer and transmits the electronic payment to the provider's financial account of choice.

The processing of prior authorization requests, as depicted in FIG. 3, begins with the entry of a prior authorization request using the provider interface portion on the provider interface computer. Typical data entry screens for the prior authorization request are shown in FIGS. 10–16. FIG. 3 shows the steps of the prior authorization data being stored in the provider database and then transmitted via push technology, either over the Internet or through dial up access, to the exchange database on the information-exchange computer.

The information-exchange system translates the prior authorization data into the insurer database format and transmits the data to the HIS over the insurer local area network. If a third party review agency located offsite handles the prior authorization requests, the data may be transmitted, over a local area network, the Internet or through dial up access, directly, or via the insurer computer, to a third party computer configured to receive the prior authorization requests and to process the prior authorization request based on the information transmitted.

The insurer or review agency processes the prior authorization request and makes a determination of approval or denial. Processed prior authorization requests are transmitted over the insurer local area network, the Internet or through POTS lines to the information-exchange computer, passing through the translator which automatically translates the processed prior authorization for storage in the exchange database. The information-exchange system then transmits approved prior authorization requests to a specialist provider interface computer, configured similarly to a provider interface computer to receive processed prior authorizations and the provider interface computer. Denied prior authorizations are preferably transmitted to the provider interface computer only.

While the present invention has been shown and described with reference to the foregoing preferred embodiment, it will be apparent to those skilled in the art that other changes in form and detail may be made therein without departing from the spirit and scope of the invention as defined in the appended claims.

I claim:

1. A system for controlling the exchange of information between an insurer and multiple health care providers in a health care delivery system, where each health care provider is assigned a subgroup of subscribers from a group of subscribers within the insurer's health plan, the system comprising:

an insurer computer configured to maintain an insurer database of subscriber insurance data on the group of the insurer's subscribers, the database having a first predetermined format;

an information-exchange computer operatively connected to the insurer computer to receive at least some subscriber insurance data on the group of the insurer's subscribers therefrom, the information-exchange computer being configured to store that subscriber insurance data in an exchange database in a second predetermined format that is different from the first predetermined format; and plural provider interface computers located at plural corresponding health care providers offices, each provider interface computer being operatively connected to the information-exchange computer to receive therefrom and store in a provider database subscriber insurance data for the subgroup of subscribers assigned to the provider, where changes in subscriber insurance data for each subgroup stored in the insurer computer are automatically transmitted to the information-exchange computer and then forwarded to the provider interface computer corresponding to the provider to whom the subgroup is assigned, to thereby automatically maintain the currency of the provider database as the subscriber insurance data changes.

2. The system of claim 1 wherein the subscriber insurance data are transmitted from the information-exchange computer to the first provider interface computer using push technology.

3. The system of claim 1 further comprising plural practice management system applications corresponding to the plural provider interface computers wherein the subscriber insurance data stored in each provider database are translated automatically and transmitted to each practice management system.

4. The system of claim 3 wherein at least one of the practice management system applications is operable on a practice management computer.

5. The system of claim 4 wherein the practice management computer communicates with the corresponding provider interface computer over a provider local area network.

6. The system of claim 3 wherein at least one of the practice management system applications is operable on one of the provider interface computers.

7. The system of claim 1 wherein the insurer database and at least one of the provider databases are mutually incompatible.

8. The system of claim 7 wherein the exchange database is ODB-compliant.

9. The system of claim 8 wherein the insurer database is not ODB-compliant.

10. The system of claim 7 wherein the exchange database is an SQL database.

11. The system of claim 10 wherein the insurer database is not an SQL database.

12. The system of claim 1 wherein at least two of the practice management systems have differing formats for the subscriber insurance data.

13. The system of claim 1 wherein at least one of the provider interface computers is configured to receive subscriber insurance data from a second information-exchange computer.

14. A system for exchanging information between an insurer providing insurance coverage to a subscriber for medical care at a health care provider, the subscriber being assigned to the health care provider and the data being exchanged over an insurer local area network and a network using an open communications protocol, the system comprising:

a first practice management system application configured to assemble claims;

a first provider computer capable of communicating on the open network, the first provider computer being configured to receive the claims from the first practice management system application, to store the claims in a first provider database and to transmit the claims over the open network;

an information-exchange computer capable of communicating on the insurer local area network and the open network, the information-exchange computer being configured to receive the claims from the first provider computer over the open network, to store the claims in an exchange database and to automatically translate and transmit the claims over the insurer local area network; and an insurer computer capable of communicating on the insurer local area network, the insurer computer being configured to receive the claims from the information-exchange computer over the insurer local area network and to store the claims in an insurer database.

15. The system of claim 14 wherein the first practice management system application is operable on a practice management computer connected to the first provider computer by a provider local area network.

16. The system of claim 15 wherein the claims are transmitted from the first practice management computer to the first provider computer over the provider local area network in an ASCII flat file.

17. The system of claim 14 wherein the first practice management system application is operable on the first provider computer.

18. The system of claim 14 further comprising a second practice management system application configured to assemble claims; and a second provider computer capable of communicating on the open network, the second provider computer being configured to receive the claims from the second practice management system application, to store the claims in a second provider database and to transmit the claims over the open network, wherein the information-exchange computer is configured to receive the claims from the second provider computer over the open network, to store the claims in an information-exchange database and to automatically translate and transmit the claims over the insurer local area network.

19. The system of claim 14 wherein the first provider database and the insurer database are mutually incompatible.

20. The system of claim 14 wherein the provider interface computer transmits the claims over the open network via push technology.

21. A system for exchanging information between an insurer providing insurance coverage to a subscriber for medical care at a health care provider, the subscriber being assigned to the health care provider and the data being exchanged over an insurer local area network and a network using an open communications protocol, the system comprising:

a first provider computer capable of communicating on the open network, the first provider computer being configured to allow a user to prepare a prior authorization request;

an information-exchange computer capable of communicating on the insurer local area network and the open network, the information-exchange computer being configured to receive the prior authorization request from the first provider computer over the open network and to store the prior authorization request in the information-exchange computer in an exchange database; and an insurer computer capable of communicating on the insurer local area network, the insurer computer being configured to receive the prior authorization from the information-exchange computer and to store the prior authorization in an insurer database, wherein the prior authorizations stored in the exchange database are translated automatically to the insurer database.

22. The system of claim 21 wherein the insurer computer is further configured to transmit via push technology a processed prior authorization to the information-exchange computer.

23. The system of claim 22 wherein the information-exchange computer transmits the processed prior authorization to the first provider computer and wherein the first provider computer is further configured to receive the processed prior authorization and to store the response in the provider database.

24. The system of claim 21 further comprising a specialist computer configured to receive the processed prior authorization and wherein the information-exchange computer transmits the processed prior authorization to the specialist computer.

* * * * *